(12) United States Patent
Sun et al.

(10) Patent No.: US 6,737,040 B1
(45) Date of Patent: May 18, 2004

(54) METHOD AND ANTIBODY FOR IMAGING BREAST CANCER

(75) Inventors: Yongming Sun, San Jose, CA (US); Herve Recipon, San Francisco, CA (US); Robert Cafferkey, San Jose, CA (US)

(73) Assignee: diaDexus, Inc., South San Francisco, CA (US)

( * ) Notice: Subject to any disclaimer, the term of this patent is extended or adjusted under 35 U.S.C. 154(b) by 0 days.

(21) Appl. No.: 09/762,027

(22) PCT Filed: Jul. 22, 1999

(86) PCT No.: PCT/US99/16811

§ 371 (c)(1),
(2), (4) Date: Aug. 6, 2001

(87) PCT Pub. No.: WO00/08210

PCT Pub. Date: Feb. 17, 2000

Related U.S. Application Data

(60) Provisional application No. 60/095,232, filed on Aug. 4, 1998.

(51) Int. Cl.[7] ...................... A61K 49/00; A61K 39/395; A61B 5/055; C12P 21/08

(52) U.S. Cl. .................. 424/9.34; 424/9.1; 424/9.341; 424/9.6; 424/142.1; 424/155.1; 424/130.1; 435/7.1; 435/7.21; 435/7.23; 530/388.1; 530/388.15; 530/389.1; 530/389.7; 530/388.8; 530/350; 536/23.5

(58) Field of Search ............... 530/350, 388.1, 530/388.15, 388.8, 389.7; 536/231, 23.5; 435/7.1, 7.21, 7.23; 424/9.1, 9.34, 9.341, 9.6, 130, 155.1, 174.1, 142.1

(56) References Cited

U.S. PATENT DOCUMENTS

| 5,668,267 A | 9/1997 | Watson et al. |
| 5,759,776 A | 6/1998 | Smith et al. |

FOREIGN PATENT DOCUMENTS

| WO | WO 98/18945 | 7/1998 |
| WO | WO 99/02559 | 1/1999 |
| WO | WO 00/08210 A1 | 2/2000 |
| WO | WO 00/43421 A1 | 7/2000 |
| WO | WO 00/60076 A2 | 10/2000 |
| WO | WO 00/62736 A2 | 10/2000 |
| WO | WO 00/73801 A2 | 12/2000 |
| WO | WO 00/78960 A2 | 12/2000 |

OTHER PUBLICATIONS

Database EMBL ebi; Aug. 6, 1995 Hillier et al.: "The WashU–Merck EST project" Database accession No. r83119 XP002205119 *abstract*.

Database EMBL ebi; Jul. 12, 1995 Hillier et al.: "The WashU–Merck EST project" Database accession No. h26328 XP002205120 *abstract*.

*Primary Examiner*—Carla J. Myers
(74) *Attorney, Agent, or Firm*—Licata & Tyrrell P.C.

(57) ABSTRACT

The present invention provides a new method of detecting, diagnosing, monitoring, staging, prognosticating, imaging and treating breast cancer.

3 Claims, No Drawings

SEQUENCE LISTING

```
<160> NUMBER OF SEQ ID NOS: 9

<210> SEQ ID NO 1
<211> LENGTH: 544
<212> TYPE: DNA
<213> ORGANISM: Homo sapiens
<220> FEATURE:
<221> NAME/KEY: unsure
<222> LOCATION: (505)..(506)
<221> NAME/KEY: unsure
<222> LOCATION: (510)
<221> NAME/KEY: unsure
<222> LOCATION: (521)
<221> NAME/KEY: unsure
<222> LOCATION: (527)..(528)
<221> NAME/KEY: unsure
<222> LOCATION: (531)
<221> NAME/KEY: unsure
<222> LOCATION: (534)..(535)
<221> NAME/KEY: unsure
<222> LOCATION: (540)..(541)

<400> SEQUENCE: 1
ctagtctcga gtctagagcg ccttgccttc tcttaggctt tgaagcattt ttgtctgtgc      60
tccctgatct tcatgtcacc accatgaagt tcttagcagt cctggtactc ttgggagttt     120
ccatctttct ggtctctgcc cagaatccga caacagctgc tccagctgac acgtatccag     180
ctactggtcc tgctgatgat gaagccctg atgctgaaac cactgctgct gcaaccactg      240
cgaccactgc tgctcctacc actgcaacca ccgctgcttc taccactgct cgtaaagaca     300
ttccagtttt acccaaatgg gttggggatc tcccgaatgg tagagtgtgt ccctgagatg     360
gaatcagctt gagtcttctg caattggtca caactattca tgcttcctgt gatttcatcc     420
aactacttac cttgcctacg atatcccctt tatctctaat cagtttattt tctttcaaat     480
aaaaaataac tatgagcaac taannaaaan aaaaaaaaaa naaaaannaa naannaaaan     540 naga                                                                 544

<210> SEQ ID NO 2
<211> LENGTH: 1066
<212> TYPE: DNA
<213> ORGANISM: Homo sapiens
<220> FEATURE:
<221> NAME/KEY: unsure
```

<222> LOCATION: (729)..(813)

<400> SEQUENCE: 2

| | | | | | |
|---|---|---|---|---|---|
| gttgaccagt | ggtcatgcca | ctgcctgttg | atttgttgaa | atattgtttt | acacgtatgt | 60 |
| tcttgttact | gattgtcaga | aagctggttt | tgagactgca | gcttggacta | aattcagtca | 120 |
| tctggctgtc | tggggaagca | tgctgaccag | tctggtgttc | tttggcatct | actcagccat | 180 |
| ctggtccacc | attctcattg | ccccaaatat | gagaggacag | aagaatggta | ccggtactgc | 240 |
| caatggagat | ggaggaagga | gacagaaaga | aacagagccc | agaccctagg | gaccaccagc | 300 |
| atttgcagaa | tggataaaca | gccttcttcc | taacaaagga | agcacagcaa | ctgtgatcct | 360 |
| gagctgtgca | cacttctggt | tgggattatt | tctggtttct | acttcctgtt | tgaagatgtg | 420 |
| gcatggagag | tgaacaagct | gctgcccacc | acctggcatc | acagcccag | aactcagcta | 480 |
| tttccatggg | accacagcat | ctcatctctg | ggctgagcca | gaaagacccc | tactgaagtc | 540 |
| cagaggcact | tttctgaaag | gctctgcttt | gacctgaagt | attttatcta | tcctcagtct | 600 |
| caggacactg | ttgatggaat | taaggccaag | cacatctgca | aaaagacat | tgctggagga | 660 |
| ggtgcaaaga | gctggaaacc | aagtctccag | tcctgggaaa | agcagtggta | tggaaaagca | 720 |
| atggaaagnn | nnnnnnnnnn | nnnnnnnnnn | nnnnnnnnnn | nnnnnnnnnn | nnnnnnnnnn | 780 |
| nnnnnnnnnn | nnnnnnnnnn | nnnnnnnnnn | nnncatagca | ccaatgacct | gaagagcctt | 840 |
| gttgaaggaa | gactccatct | gatgactcag | agcaagtatt | ttttagtgtg | ttattgttat | 900 |
| tagcagaaag | agggccataa | aatacatggg | gcaagctgaa | tatatcttag | gcaaaagaag | 960 |
| aaaatattca | aattcttatg | ttattttatc | taattatttt | atctcttttt | gtgtgtgact | 1020 |
| tataatgtgt | gtattgtatt | aataaaagta | tataaacatg | tagttt | | 1066 |

<210> SEQ ID NO 3
<211> LENGTH: 649
<212> TYPE: DNA
<213> ORGANISM: Homo sapiens

<400> SEQUENCE: 3

| | | | | | |
|---|---|---|---|---|---|
| gcaatgttta | atatctcata | agctatacac | acctcgaagc | catcaatgac | aacctttct | 60 |
| tgctgaatag | aacagtgatt | gatgtcatga | agacaatttt | atctcctttt | gccttccata | 120 |
| atttgtacca | ggttatataa | tagtataaca | ctgccaagga | gcggattatc | tcatcttcat | 180 |
| cctgtaattc | cagtgtttgt | cacgtggttg | ttgaataaat | gaataaagaa | tgagaaaacc | 240 |
| agaagctctg | atacataatc | ataatgataa | ttatttcaat | gcacaactac | gggtggtgct | 300 |
| gaactagaat | ctatattttc | tgaaactggc | tcctctagga | tctactaatg | atttaaatct | 360 |
| aaaagatgaa | gttagtaaag | catcagaaaa | aaaaggtaaa | caaattgctc | ctgtggagat | 420 |
| gattggcatc | acatggtgtt | ttgagctgat | acacccaaca | cttgagctca | ctgcaacagt | 480 |
| accagatttt | caccgctatg | cctcctttca | ctctgggagt | cttccagagg | tcttgcactc | 540 |
| gggagagcat | gctcaggttt | ccccagctct | acaaaatcac | ccagaatgcc | aaagacttca | 600 |
| acacaagggt | aaataaggtt | gatctcagaa | ttgtcacctc | aaaaaggcc | | 649 |

<210> SEQ ID NO 4
<211> LENGTH: 388
<212> TYPE: DNA
<213> ORGANISM: Homo sapiens
<220> FEATURE:
<221> NAME/KEY: unsure
<222> LOCATION: (378)
<221> NAME/KEY: unsure

```
<222> LOCATION: (385)

<400> SEQUENCE: 4
agctgctcaa tacggaacat attctcagtc ctcctctggt ctacaaagcc tgtgatttct      60
tgtctatgga cagaacgtct ggtttaatct acaggaaccc ataacttcct gaagctttat     120
gcttaacagt gacaacgtga gtcagttgaa ttttattgtg tttcagtccg tagagtatta    180
gctaacagaa acctttccat tgccatactg agaaactggc agcaggcagt gtgcctacag     240
gtctacaaag aaacttcaga tcatcttctt gagggaaaga agctgaagtg ctacataaga    300
tgcttgtgct tcataactct cagaagctgc agattctgta taaatcctta gaaaagagca    360 tccectgaat ccataaangt atatngcg                                        388

<210> SEQ ID NO 5
<211> LENGTH: 1227
<212> TYPE: DNA
<213> ORGANISM: Homo sapiens
<220> FEATURE:
<221> NAME/KEY: unsure
<222> LOCATION: (327)
<221> NAME/KEY: unsure
<222> LOCATION: (352)
<221> NAME/KEY: unsure
<222> LOCATION: (369)
<221> NAME/KEY: unsure
<222> LOCATION: (850)..(880)
<221> NAME/KEY: unsure
<222> LOCATION: (1220)

<400> SEQUENCE: 5
attttgtagt tcagcaaatc ctccaaatac acagcatgtt acaaggcact ggtggcacag      60
ggcacaacag gaaatgatat ttatttagca aattcattta acaaatatta ttgggcacct    120
gttatgtgag acactgtcct aggcactgtg ggataacaac agcaaacact tcacacaaca    180
gcctggcctt cctgtgtttt acaacagctc ctaaagatag ctgatatcaa gacatttgag    240
ggacacagtt catgtagaat caaaatatta gtatttcaga ataaggattt tttttctgaa    300
aagcatacag agaggaaaca gcttaanaat aggtcaagac ctaaaaacag antataatca    360
cggaataanc tggataaccc agacagtccc cacagaattt ctttcaggtc acagatttct    420
taaaactcac ccccaaaatg tgcctgcttg gttgtttgaa tcttgcataa ttaatgtcac    480
aggcgcaagc cgctgaactt agttgagatg cagaaaacaa acaaatgcaa tgacatatct    540
gagaagcatt tatgtaactc cggttaagtg gtgaggaggg gtgtgtgaag acagtgtgca    600
tgcatgagtg tgtattcata tatatgtgta tacatatgaa tttcactgtt attttccagg    660
gtctatggac aatgtggcag taagagtcta tgatgttctg aaacttttca cagtaaatcc    720
aaagattaca gaccttacaa ggtgcttgca ttctgttgct tttccatctg tcacttctca    780
ggttatttga ctgtgttcaa accttctttt ctttttcatt gagtttcatt ttttaagctt    840
gttaaatgcn nnnnnnnnn nnnnnnnnnn nnnnnnnnn tgtcattttt cacattatcc    900
tctcttctct gcaacaagga tagtaagatg tagatgaatg caaaaataat aacaacaata    960
aggaaatata ttaaagcttt aaaatatgca catatgtagt tctaaagagc aataacggta   1020
gtatctattt cgaacatgca ttaggcaaaa agaaatcaa aactgaaatt ttcgtgtatt    1080
tttccccttg taagatgttc aaatgctaac ttcattttct cctttcctct atgtggcact   1140
ttctcaaaat atctatgaaa tacttttaga caaagattga gctggagaaa gagatacaaa   1200
tttccatccc cccagacagn gagacat                                        1227
```

<210> SEQ ID NO 6
<211> LENGTH: 253
<212> TYPE: DNA
<213> ORGANISM: Homo sapiens
<220> FEATURE:
<221> NAME/KEY: unsure
<222> LOCATION: (181)
<221> NAME/KEY: unsure
<222> LOCATION: (201)
<221> NAME/KEY: unsure
<222> LOCATION: (205)
<221> NAME/KEY: unsure
<222> LOCATION: (238)
<221> NAME/KEY: unsure
<222> LOCATION: (241)..(242)
<221> NAME/KEY: unsure
<222> LOCATION: (250)

<400> SEQUENCE: 6

```
gaacagcctc acttgtgttg ctgtcagtgc cagtagggca ggcaggaatg cagcagagag       60
gactcgccat cgtggccttg gctgtctgtg cggccctaca tgcctcagaa gccatacttc      120
ccattgcctc cagctgttgc acggaggttt cacatcatat ttccagaagg ctcctggaaa      180
nagtgaatat gtgtcgcatc naganagctg atggggattg tgacttggct gctgtcancc      240
nncatgtcan gcg                                                         253
```

<210> SEQ ID NO 7
<211> LENGTH: 943
<212> TYPE: DNA
<213> ORGANISM: Homo sapiens
<220> FEATURE:
<221> NAME/KEY: unsure
<222> LOCATION: (128)
<221> NAME/KEY: unsure
<222> LOCATION: (130)
<221> NAME/KEY: unsure
<222> LOCATION: (925)

<400> SEQUENCE: 7

```
gggggcctgg ccccggcccc tgtgaggacc ccgcgggtgc tggggtaaga ggctctagac       60
ccttcacctg tcagtcacct gagggaggct gaggccaagc ccatccctc agaatcaagg      120 cttgcaancn ccctcacct gcccagtctc tgtccacacc cctcgggctg aagacggccc      180
tgaccaggcc ctgggcctca gcgaccaccc ctcccctcc tgcctggacc cagggagcag      240
gtgcaggggg ctccgagccc ctggtgactg tcaccgtgca gtcgccttc acagtggccc      300 tgagggcacg aagaggagcc gacctgtcca gcctgcgggc actgctgggc caagccctcc      360
ctcaccaggc ccagcttggg caactcaggt gggccagaaa gccccggtg gctgcggtgg      420 agctgggcac cgccccgact gaggcagctg ctggaagagg gggtggcaga ggtcactgcc      480
ctccctgcag gccccaccca ggaggccccc tctgaggaat ctctttgcag ttacctagcc      540
ccaggtgagg acgggcactg gtccccatc cccgaggagg agtcgctgca gagggcctgg      600
caggacgcag ctgcctgccc caggggctg cagctgcagt gcaggggagc cggggtcgg      660 ccggtcctct accaggtggt ggcccagcac agctactccg cccagggcc agaggacctg      720 ggcttccgac aggggacac ggtggacgtc ctgtgtgaag tggaccaggc atggctggag      780
ggccactgtg acgccgcat cggcatcttc cccaagtgct tcgtggtccc cgccggccct      840
cggatgtcag gagccccgg ccgcctgccc cgatcccagc agggagatca gccctaatga      900
tgctgtgtcc atgatgcttt taatnaaaaa aacccccact gca                        943
```

```
-continued

<210> SEQ ID NO 8
<211> LENGTH: 249
<212> TYPE: DNA
<213> ORGANISM: Homo sapiens
<220> FEATURE:
<221> NAME/KEY: unsure
<222> LOCATION: (48)
<221> NAME/KEY: unsure
<222> LOCATION: (110)
<221> NAME/KEY: unsure
<222> LOCATION: (192)
<221> NAME/KEY: unsure
<222> LOCATION: (205)
<221> NAME/KEY: unsure
<222> LOCATION: (218)

<400> SEQUENCE: 8
atcacattaa gtcattgcta attttataaa caaaaacaat ggttttantt tgcatctccc      60
tgattggtat tgctgtagaa catatttgga gaagtttgtt tgtctttggn gtttatttca     120
tgaatagatt gtgtgcccat tttctcttgg ggtattcagt tttttattac tgatgtgagc     180
atgtgtatgg gngattattt gatgnttatc agttttgntt agtagactgg caatatttag     240
tcttgctgt                                                             249

<210> SEQ ID NO 9
<211> LENGTH: 690
<212> TYPE: DNA
<213> ORGANISM: Homo sapiens

<400> SEQUENCE: 9
gacgcccagt gacctgccga ggtcggcagc acagagctct ggagatgaag accctgttcc      60
tgggtgtcac gctcggcctg gccgctgccc tgtccttcac cctggaggag gaggatatca     120
cagggacctg gtacgtgaag gccatggtgg tcgataagga ctttccggag gacaggaggc     180
ccaggaaggt gtccccagtg aaggtgacag ccctgggcgg tgggaagttg gaagccacgt     240
tcaccttcat gagggaggat cggtgcatcc agaagaaaat cctgatgcgg aagacggagg     300
agcctggcaa atacagcgcc tatggggggca ggaagctcat gtacctgcag gagctgccca     360
ggagggacca ctacatcttt tactgcaaag accagcacca tgggggcctg ctccacatgg     420
gaaagcttgt gggtaggaat tctgatacca accgggaggc cctggaagaa tttaagaaat     480
tggtgcagcg caagggactc tcggaggagg acattttcac gcccctgcag acgggaagct     540
gcgttcccga acactaggca gcccccgggt ctgcacctcc agagcccacc ctaccaccag     600
acacagagcc cggaccacct ggacctaccc tccagccatg acccttccct gctcccaccc     660
acctgactcc aaataaagtc cttctccccc                                      690
```

METHOD AND ANTIBODY FOR IMAGING BREAST CANCER

This application claims benefit of application Ser. No. 60/095,232 filed Aug. 4, 1998.

FIELD OF THE INVENTION

This invention relates, in part, to newly developed assays for detecting, diagnosing, monitoring, staging, prognosticating, imaging and treating cancers, particularly breast cancer.

BACKGROUND OF THE INVENTION

One of every nine American women will develop breast cancer sometime during her life based on a lifespan of 85 years. Annually, over 180,000 women in the United States will be diagnosed with breast cancer and approximately 46,000 will die of the disease.

Every woman is at risk for breast cancer. A woman's chances of developing breast cancer increase as she grows older; 80 percent of all cancers are found in women over the age of 50. There are also several risk factors that can increase a woman's chances of developing cancer. A woman may be at increased risk if she has a family history of the disease, if she had her first child after the age of 30 or has no children, or if she began menstruating early.

However, more than 70 percent of women who develop breast cancer have no known risk factors. Less than 10 percent of breast cancer cases are thought to be related to the BRCA1 gene discovered in 1994. Researchers are now investigating the role other factors such as nutrition, alcohol, exercise, smoking, and oral contraceptives may play in cancer prevention.

As with many other cancers, the best chance for successful treatment occurs when breast cancer is found early. Mammograms, special x-rays of the breast, can detect more than 90 percent of all breast cancers. If breast cancer is found early, the chance of cure is greater than 90 percent. Treatment options include surgery, chemotherapy, and radiation therapy depending on the stage of the cancer.

Procedures used for detecting, diagnosing, monitoring, staging, prognosticating and imaging breast cancer are of critical importance to the outcome of the patient. Patients diagnosed with early breast cancer generally have a much greater five-year survival rate as compared to the survival rate for patients diagnosed with distant metastasized breast cancer. New diagnostic methods which are more sensitive and specific for detecting early breast cancer are clearly needed.

Breast cancer patients are closely monitored following initial therapy and during adjuvant therapy to determine response to therapy and to detect persistent or recurrent disease of metastasis. There is clearly a need for a breast cancer marker which is more sensitive and specific in detecting breast cancer and its recurrence and progression.

Another important step in managing breast cancer is to determine the stage of the patient's disease. Stage determination has potential prognostic value and provides criteria for designing optimal therapy. Generally, pathological staging of breast cancer is preferable over clinical staging because the former gives a more accurate prognosis. However, clinical staging would be preferred were it at least as accurate as pathological staging because it does not depend on an invasive procedure to obtain tissue for pathological evaluation. Staging of breast cancer would be improved by detecting new markers in cells, tissues, or bodily fluids which could differentiate between different stages of invasion.

In the present invention methods are provided for detecting, diagnosing, monitoring, staging, prognosticating, imaging and treating breast cancer via 9 Breast Specific Genes (BSGs). The 9 BSGs refer, among other things, to native proteins expressed by the genes comprising the polynucleotide sequences of any of SEQ ID NO: 1–9. In the alternative, what is meant by the 9 BSGs as used herein, means the native mRNAs encoded by the genes comprising any of the polynucleotide sequences of SEQ ID NO: 1–9 or it can refer to the actual genes comprising any of the polynucleotide sequences of SEQ ID NO: 1–9.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide a method for diagnosing the presence of breast cancer by analyzing for changes in levels of BSG in cells, tissues or bodily fluids compared with levels of BSG in preferably the same cells, tissues, or bodily fluid type of a normal human control, wherein a change in levels of BSG in the patient versus the normal human control is associated with breast cancer.

Further provided is a method of diagnosing metastatic breast cancer in a patient having such cancer which is not known to have metastasized by identifying a human patient suspected of having breast cancer that has metastasized; analyzing a sample of cells, tissues, or bodily fluid from such patient for BSG; comparing the BSG levels in such cells, tissues, or bodily fluid with levels of BSG in preferably the same cells, tissues, or bodily fluid type of a normal human control, wherein a change in BSG levels in the patient versus the normal human control is associated with a cancer which has metastasized.

Also provided by the invention is a method of staging breast cancer in a human which has such cancer by identifying a human patient having such cancer; analyzing a sample of cells, tissues, or bodily fluid from such patient for BSG; comparing BSG levels in such cells, tissues, or bodily fluid with levels of BSG in preferably the same cells, tissues, or bodily fluid type of a normal human control sample, wherein a change in BSG levels in the patient versus the normal human control is associated with a cancer which is progressing or regressing or in remission.

Further provided is a method of monitoring breast cancer in a human having such cancer for the onset of metastasis. The method comprises identifying a human patient having such cancer that is not known to have metastasized; periodically analyzing a sample of cells, tissues, or bodily fluid from such patient for BSG; comparing the BSG levels in such cells, tissue, or bodily fluid with levels of BSG in preferably the same cells, tissues, or bodily fluid type of a normal human control sample, wherein a change in BSG levels in the patient versus the normal human control is associated with a cancer which has metastasized.

Further provided is a method of monitoring the change in stage of breast cancer in a human having such cancer by looking at levels of BSG in a human having such cancer. The method comprises identifying a human patient having such cancer; periodically analyzing a sample of cells, tissues, or bodily fluid from such patient for BSG; comparing the BSG levels in such cells, tissue, or bodily fluid with levels of BSG in preferably the same cells, tissues, or bodily fluid type of a normal human control sample, wherein a change in BSG levels in the patient versus the normal human control is associated with a cancer which is progressing or regressing or in remission.

Further provided are antibodies against the BSGs or fragments of such antibodies which can be used to detect or image localization of the BSGs in a patient for the purpose of detecting or diagnosing a disease or condition. Such antibodies can be polyclonal or monoclonal, or prepared by molecular biology techniques. The term "antibody", as used herein and throughout the instant specification is also meant to include aptamers and single-stranded oligonucleotides such as those derived from an in vitro evolution protocol referred to as SELEX and well known to those skilled in the art. Antibodies can be labeled with a variety of detectable labels including, but not limited to, radioisotopes and paramagnetic metals. These antibodies or fragments thereof can also be used as therapeutic agents in the treatment of diseases characterized by expression of a BSG. In therapeutic applications, the antibody can be used without or with derivatization to a cytotoxic agent such as a radioisotope, enzyme, toxin, drug or a prodrug.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DESCRIPTION OF THE INVENTION

The present invention relates to diagnostic assays and methods, both quantitative and qualitative for detecting, diagnosing, monitoring, staging, prognosticating and imaging cancers by comparing levels of BSG with those of BSG in a normal human control. What is meant by levels of BSG as used herein, means levels of the native protein expressed by the genes comprising the polynucleotide sequence of any of SEQ ID NO: 1–9. In the alternative, what is meant by levels of BSG as used herein, means levels of the native mRNA encoded by any of the genes comprising any of the polynucleotide sequences of SEQ ID NO: 1–9 or levels of the gene comprising any of the polynucleotide sequence of SEQ ID NO: 1–9. Such levels are preferably measured in at least one of, cells, tissues and/or bodily fluids, including determination of normal and abnormal levels. Thus, for instance, a diagnostic assay in accordance with the invention for measuring changes in levels of any one of the BSG proteins compared to normal control bodily fluids, cells, or tissue samples may be used to diagnose the presence, of cancers, including breast cancer. By "change" it is meant either an increase or decrease in levels of the BSG. For example, for BSGs such as Mam001 (SEQ ID NO:2), Mam004 (SEQ ID NO:4) and Mam005 (SEQ ID NO:3), an increase in levels as compared to ,normal human controls is associated with breast cancer, metastasis and progression of the cancer, while a decrease in levels is association with regression and/or remission. For the BSG Mam002 (SEQ ID NO:1), a decrease in levels as compared to normal human controls is associated with breast cancer, metastasis and progression while an increase is associated with regression and/or remission. Any of the 9 BSGs may be measured alone in the methods of the invention, or all together or any combination of the nine.

All the methods of the present invention may optionally include measuring the levels of other cancer markers as well as BSG. Other cancer markers, in addition to BSG, such as BRCA1 are known to those of skill in the art.

Diagnostic Assays

The present invention provides methods for diagnosing the presence of breast cancer by analyzing for changes in levels of BSG in cells, tissues or bodily fluids compared with levels of BSG in cells, tissues or bodily fluids of preferably the same type from a normal human control, As demonstrated herein an increase in levels of BSGs such as Mam001 (SEQ ID NO:2), Mam004 (SEQ ID NO:4) or Mam005 (SEQ ID NO:3) in the patient versus the normal human control is associated with the presence of breast cancer, while a decrease in levels of BSGs such as Mam002 (SEQ ID NO:1) in the patient versus the normal human control is associated with the presence of breast cancer.

Without limiting the instant invention, typically, for a quantitative diagnostic assay a positive result indicating the patient being tested has cancer is one in which cells, tissues, or bodily fluid levels of the cancer marker, such as BSG, are at least two times higher or lower, and most preferably are at least five times higher or lower, than in preferably the same cells, tissues, or bodily fluid of a normal human control.

The present invention also provides a method of diagnosing metastatic breast cancer in a patient having breast cancer which has not yet metastasized for the onset of metastasis. In the method of the present invention, a human cancer patient suspected of having breast cancer which may have metastasized (but which was not previously known to have metastasized) is identified. This is accomplished by a variety of means known to those of skill in the art. For example, in the case of breast cancer, patients are typically diagnosed with breast cancer following traditional detection methods.

In the present invention, determining the presence of BSG level in cells, tissues, or bodily fluid, is particularly useful for discriminating between breast cancer which has not metastasized and breast cancer which has metastasized. Existing techniques have difficulty discriminating between breast cancer which has metastasized and breast cancer which has not metastasized and proper treatment selection is often dependent upon such knowledge.

In the present invention, the cancer marker levels measured in such cells, tissues, or bodily fluid is BSG, and are compared with levels of BSG in preferably the same cells, tissue, or bodily fluid type of a normal human control. That is, if the cancer marker being observed is just BSG in serum, this level is preferably compared with the level of BSG in serum of a normal human patient. An increase in BSGs such as Mam001 (SEQ ID NO:2), Mam004 (SEQ ID NO:4) or Mam005 (SEQ ID NO:3) in the patient versus the normal human control is associated with breast cancer which has metastasized while a decrease in BSGs such as Mam002 (SEQ ID NO:1) in the patient versus the normal human control is associated with breast cancer which has metastasized.

Without limiting the instant invention, typically, for a quantitative diagnostic assay a positive result indicating the cancer in the patient being tested or monitored has metastasized is one in which cells, tissues, or bodily fluid levels of the cancer marker, such as BSG, are at least two times higher or lower, and most preferably are at least five times higher or lower, than in preferably the same cells, tissues, or bodily fluid of a normal patient.

Normal human control as used herein includes a human patient without cancer and/or non cancerous samples from the patient; in the methods for diagnosing or monitoring for metastasis, normal human control preferably comprises samples from a human patient that is determined by reliable methods to have breast cancer which has not metastasized, such as earlier samples of the same patient.

Staging

The invention also provides a method of staging breast cancer in a human patient.

The method comprises identifying a human patient having such cancer; analyzing a sample of cells, tissues, or bodily fluid from such patient for BSG. Then, the method compares BSG levels in such cells, tissues, or bodily fluid with levels of BSG in preferably the same cells, tissues, or bodily fluid type of a normal human control sample, wherein an increase in levels of BSGs such as Mam001 (SEQ ID NO:2), Mam004 (SEQ ID NO:4) or Mam005 (SEQ ID NO:3) or a decrease in levels of BSGs such as Mam002 (SEQ ID NO:1) in the patient versus the normal human control is associated with a cancer which is progressing and a decrease in levels of BSGs such as Mam001 (SEQ ID NO:2), Mam004 (SEQ ID NO:4) or Mam005 (SEQ ID NO:3) or an increase in levels of BSGs such as Mam002 (SEQ ID NO:1) is associated with a cancer which is regressing or in remission.

Monitoring

Further provided is a method of monitoring breast cancer in a human having such cancer for the onset of metastasis. The method comprises identifying a human patient having such cancer that is not known to have metastasized; periodically analyzing a sample of cells, tissues, or bodily fluid from such patient for BSG; comparing the BSG levels in such cells, tissue, or bodily fluid with levels of BSG in preferably the same cells, tissues, or bodily fluid type of a normal human control sample, wherein an increase in levels of BSGs such as Mam001 (SEQ ID NO:2), Mam004 (SEQ ID NO:4) or Mam005 (SEQ ID NO:3) or a decrease in levels of BSGs such as Mam002 (SEQ ID NO:1) in the patient versus the normal human control is associated with a cancer which has metastasized.

Further provided by this invention is a method of monitoring the change in stage of breast cancer in a human having such cancer. The method comprises identifying a human patient having such cancer; periodically analyzing a sample of cells, tissues, or bodily fluid from such patient for BSG; comparing the BSG levels in such cells, tissue, or bodily fluid with levels of BSG in preferably the same cells, tissues, or bodily fluid type of a normal human control sample, wherein an increase in levels of BSGs such as Mam001 (SEQ ID NO:2), Mam004 (SEQ ID NO:4) or Mam005 (SEQ ID NO:3) or a decrease in levels of BSGs such as Mam002 (SEQ ID NO:1) in the patient versus the normal human control is associated with a cancer which is progressing in stage and a decrease in the levels of BSGs such as Mam001 (SEQ ID NO:2), Mam004 (SEQ ID NO:4) or Mam005 (SEQ ID NO:3) or an increase in levels of BSGs such as Mam002 (SEQ ID NO:1) is associated with a cancer which is regressing in stage or in remission.

Monitoring such patient for onset of metastasis is periodic and preferably done on a quarterly basis, However, this may be more or less frequent depending on the cancer, the particular patient, and the stage of the cancer.

Assay Techniques

Assay techniques that can be used to determine levels of gene expression, such as BSG of the present invention, in a sample derived from a host are well-known to those of skill in the art. Such assay methods include radioimmunoassays, reverse transcriptase PCR (RT-PCR) assays, immunohistochemistry assays, in situ hybridization assays, competitive-binding assays, Western Blot analyses, ELISA assays and proteomic approaches. Among these, ELISAs are frequently preferred to diagnose a gene's expressed protein in biological fluids.

An ELISA assay initially comprises preparing an antibody, if not readily available from a commercial source, specific to BSG, preferably a monoclonal antibody. In addition a reporter antibody generally is prepared which binds specifically to BSG. The reporter antibody is attached to a detectable reagent such as radioactive, fluorescent or enzymatic reagent, for example horseradish peroxidase enzyme or alkaline phosphatase.

To carry out the ELISA, antibody specific to BSG is incubated on a solid support, e.g. a polystyrene dish, that binds the antibody. Any free protein binding sites on the dish are then covered by incubating with a non-specific protein such as bovine serum albumin. Next, the sample to be analyzed is incubated in the dish, during which time BSG binds to the specific antibody attached to the polystyrene dish. Unbound sample is washed out with buffer. A reporter antibody specifically directed to BSG and linked to horseradish peroxidase is placed in the dish resulting in binding of the reporter antibody to any monoclonal antibody bound to BSG. Unattached reporter antibody is then washed out. Reagents for peroxidase activity, including a colorimetric substrate are then added to the dish. Immobilized peroxidase, linked to BSG antibodies, produces a colored reaction product. The amount of color developed in a given time period is proportional to the amount of BSG protein present in the sample. Quantitative results typically are obtained by reference to a standard curve.

A competition assay may be employed wherein antibodies specific to BSG attached to a solid support and labeled BSG and a sample derived from the host are passed over the solid support and the amount of label detected attached to the solid support can be correlated to a quantity of BSG in the sample.

Nucleic acid methods may be used to detect BSG mRNA as a marker for breast cancer. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e., gridding) can be used to both detect the expression of and quantitate the level of expression of that gene. In this approach, a cDNA encoding the BSG gene is fixed to a substrate. The substrate may be of any suitable type including but not limited to glass, nitrocellulose, nylon or plastic. At least a portion of the DNA encoding the BSG gene is attached to the substrate and then incubated with the analyte, which may be RNA or a complementary DNA (cDNA) copy of the RNA, isolated from the tissue of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

Of the proteomic approaches, 2D electrophoresis is a technique well known to those in the art. Isolation of individual proteins from a sample such as serum is accomplished using sequential separation of proteins by different characteristics usually on polyacrylamide gels. First, proteins are separated by size using an electric current. The current acts uniformly on all proteins, so smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot. Analysis of the spots with chemical or antibody probes, or subsequent protein microsequencing can reveal the relative abundance of a given protein and the identity of the proteins in the sample.

The above tests can be carried out on samples derived from a variety of patients' cells, bodily fluids and/or tissue extracts (homogenates or solubilized tissue) such as from tissue biopsy and autopsy material. Bodily fluids useful in the present invention include blood, urine, saliva, or any other bodily secretion or derivative thereof. Blood can include whole blood, plasma, serum, or any derivative of blood.

In Vivo Antibody Use

Antibodies against BSGs can also be used in vivo in patients with disease of the breast. Specifically, antibodies against a BSG can be injected into a patient suspected of having a disease of the breast for diagnostic and/or therapeutic purposes. The use of antibodies for in vivo diagnosis is well known in the art. For example, antibody-chelators labeled with Indium-111 have been described for use in the radioimmunoscintographic imaging of carcinoembryonic antigen expressing tumors (Sumerdon et al. Nucl. Med. Biol. 1990 17:247–254). In particular, these antibody-chelators have been used in detecting tumors in patients suspected of having recurrent colorectal cancer (Griffin et al. J. Clin. Onc. 1991 9:631–640). Antibodies with paramagnetic ions as labels for use in magnetic resonance imaging have also been described (Lauffer, R. B. Magnetic Resonance in Medicine 1991 22:339–342). Antibodies directed against BSGs can be used in a similar manner. Labeled antibodies against a BSG can be injected into patients suspected of having a disease of the breast such as breast cancer for the purpose of diagnosing or staging of the disease status of the patient. The label used will be selected in accordance with the imaging modality to be used. For example, radioactive labels such as Indium-111, Technetium-99m or Iodine-131 can bemused for planar scans or single photon emission computed tomography (SPECT). Positron emitting labels such as Fluorine-19 can be used in positron emission tomography. Paramagnetic ions such as Gadlinium (III) or Manganese (II) can used in magnetic resonance imaging (MRI). Localization of the label within the breast or external to the breast permits determination of the spread of the disease. The amount of label within the breast also allows determination of the presence or absence of cancer in the breast.

For patients diagnosed with breast cancer, injection of an antibody against a BSG can also have a therapeutic benefit. The antibody may exert its therapeutic effect alone. Alternatively, the antibody is conjugated to a cytotoxic agent such as a drug, toxin or radionuclide to enhance its therapeutic effect. Drug monoclonal antibodies have been described in the art for example by Garnett and Baldwin, Cancer Research 1986 46:2407–2412. The use of toxins conjugated to monoclonal antibodies for the therapy of various cancers has also been described by Pastan et al. Cell 1986 47:641–648). Yttrium-90 labeled monoclonal antibodies have been described for maximization of dose delivered to the tumor while limiting toxicity to normal tissues (Goodwin and Meares Cancer Supplement 1997 80:2675–2680). Other cytotoxic radionuclides including, but not limited to Copper-67, Iodine-131 and Rhenium-186 can also be used for labeling of antibodies against BSGs.

Antibodies which can be used in these in vivo methods include both polyclonal and monoclonal antibodies and antibodies prepared via molecular biology techniques. Antibody fragments and aptamers and single-stranded oligonucleotides such as those derived from an in vitro evolution protocol referred to as SELEX and well known to those skilled in the art can also be used.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

Example 1

Identification of BSGs were carried out by a systematic analysis of data in the LIFESEQ database available from Incyte Pharmaceuticals, Palo Alto, Calif., using the data mining Cancer Leads Automatic Search Package (CLASP) developed by diaDexus LLC, Santa Clara, Calif.

The CLASP performs the following steps:

Selection of highly expressed organ specific genes based on the abundance level of the corresponding EST in the targeted organ versus all the other organs.

Analysis of the expression level of each highly expressed organ specific genes in normal, tumor tissue, disease tissue and tissue libraries associated with tumor or disease.

Selection of the candidates demonstrating component ESTs were exclusively or more frequently found in tumor libraries.

CLASP allows the identification of highly expressed organ and cancer specific genes useful in the diagnosis of breast cancer.

TABLE 1

BSQs Sequences

| SEQ ID NO: | LS Clone ID | LSA Gene ID |
|---|---|---|
| 1 | 2740238(Mam002) | 242151 |
| 2 | 1730886(Mam001) | 238469 |
| 3 | y155b03(Mam005) | 348845 |
| 4 | 2613064(Mam004) | 27052 |
| 5 | 894184 | 221086 |
| 6 | 2299454 | 27681 |
| 7 | 2258254 | 248176 |
| 8 | 789767 | 156580 |
| 9 | 1213903 | 219737 |

The following example was carried out using standard techniques, which are well known and routine to those of skill in the art, except where otherwise described in detail. Routine molecular biology techniques of the following example can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Example 2

Relative Quantitation of Gene Expression

Real-time quantitative PCR with fluorescent Taqman probes is a quantitative detection system utilizing the 5'–3' nuclease activity of Taq DNA polymerase. The method uses an internal fluorescent oligonucleotide probe (Taqman) labeled with a 5' reporter dye and a downstream, 3' quencher dye. During PCR, the 5'–3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control was used to standardize the amount of sample RNA added to the reaction and normalize for Reverse Transcriptase (RT) efficiency. Either cyclophilin, glyceraldehyde-3-phosphate dehydrogenase (GAPDH) or 18S ribosomal RNA (rRNA) was used as this endogenous control. To calculate relative Quantitation between all the samples studied, the target RNA levels for one sample were used as the basis for comparative results (calibrator). Quantitation relative to the "calibrator" can be obtained using the standard curve method or the comparative method (User Bulletin #2: ABI PRISM 7700 Sequence Detection System). To evaluate the tissue distribution, and the level of breast specific markers (BSM) Mam001 (SEQ ID NO:2), Mam002 (SEQ ID NO:1), Mam004 (SEQ ID NO:4) and Mam005 (SEQ ID NO:3) in normal and cancer tissue, total RNA was extracted from cancer and matched normal adjacent tissues (NAT) and from unmatched cancer and normal tissues. Subsequently, first strand cDNA was prepared with reverse transcriptase and the polymerase chain reaction carried out using primers and Taqman probes specific to each of Mam001 (SEQ ID NO:2), Mam002 (SEQ ID NO:1), Mam004 (SEQ ID NO:4) and Mam005 (SEQ ID NO:3) respectively. The results are obtained using the ABI PRISM 7700 Sequence Detector. The numbers are relative levels of expression of Mam001 (SEQ ID NO:2), Mam002 (SEQ ID NO:1), Mam004 (SEQ ID NO:4) and Mam005 (SEQ ID NO:3) compared to their respective calibrators.

Measurement of SEQ ID NO:2; Clone ID;1730886 Gene ID: 238469 (Mam001)

The numbers depicted in Table 2 are relative levels of expression in 12 normal tissues of Mam001 (SEQ ID NO:2) compared to testis (calibrator). These RNA samples were obtained commercially and were generated by pooling samples from a particular tissue from different individuals.

TABLE 2

Relative levels of Mam001 (SEQ ID NO:2) Expression in Pooled Samples

| Tissue | NORMAL |
|---|---|
| Brain | 0 |
| Heart | 0 |
| Kidney | 0 |
| Liver | 0 |
| Lung | 0 |
| Mammary | 6 |
| Prostate | 0 |
| Muscle | 0 |
| Small Intestine | 0 |
| Testis | 1 |
| Thymus | 0 |
| Uterus | 0 |

The relative levels of expression in Table 2 show that Mam001 (SEQ ID NO:2) mRNA expression is detected in the pool of normal mammary and in testis but not in the other 10 normal tissue pools analyzed. These results demonstrate that Mam001 (SEQ ID NO:2) mRNA expression is highly specific for mammary tissue and is also found in testis. Expression in a male specific tissue is not relevant in detecting cancer in female specific tissues The tissues shown in Table 2 are pooled samples from different individuals. The tissues shown in Table 3 were obtained from individuals and are not pooled. Hence the values for mRNA expression levels shown in Table 2 cannot be directly compared to the values-shown in Table 3.

The numbers depicted in Table 3 are relative levels of expression of Mam001 (SEQ ID NO:2) compared to testis (calibrator), in 24 pairs of matching samples. Each matching pair contains the cancer sample for a particular tissue and the normal adjacent tissue (NAT) sample for that same tissue from the same individual.

TABLE 3

Relative levels of Mam001 (SEQ ID NO:2) Expression in Individual Samples

| Sample ID | Tissue | Cancer | Matching Normal |
|---|---|---|---|
| Mam 47XP | Mammary Gland | 0 | 0 |
| Mam A06X | Mammary Gland | 23 | 1 |
| Mam B011X | Mammary Gland | 0 | 5 |
| Mam 603X/C034 | Mammary Gland | 0 | 2.10 |
| Mam 162X | Mammary Gland | 1.96 | 0.15 |
| Mam 42DN | Mammary Gland | 0.38 | 1.27 |
| Mam S079 | Mammary Gland | 0.34 | 0.36 |
| Mam S123 | Mammary Gland | 0.03 | 0.87 |
| Mam S516 | Mammary Gland | 0.43 | 0.53 |
| Mam S699 | Mammary Gland | 0.40 | 0.66 |
| Mam 5997 | Mammary Gland | 0.41 | 0.51 |
| Sto AC44 | Stomach | 0 | 0 |
| TST 39X | Testis | 0 | 0 |
| Cln SG45 | Colon | 0 | 0 |
| Cln TX01 | Colon | 0 | 0 |
| Cvx NK23 | Cervix | 0 | 0 |

TABLE 3-continued

Relative levels of Mam001 (SEQ ID NO:2) Expression in Individual Samples

| Sample ID | Tissue | Cancer | Matching Normal |
|---|---|---|---|
| Cvx NK24 | Cervix | 0 | 0 |
| Endo 3AX | Endometrium | 0 | 0 |
| Hnd6 4XA | Endometrium | 0 | 0 |
| Endo 5XA | Endometrium | 0 | 0 |
| Kid 11XD | Kidney | 0 | 0 |
| Kid 5XD | Kidney | 0 | 0 |
| Lng C20X | Lung | 0 | 0 |
| Lng SQ56 | Lung | 0 | 0 |

Among 48 samples in Table 3 representing 8 different tissues expression is seen only in mammary tissues. These results confirm the tissue specificity results obtained with normal samples shown in Table 2. Table 2 and Table 3 represents a combined total of 60 samples in 16 human tissue types. Thirty-six samples representing 14 different tissue types excluding breast and testis had no detected Mam001 (SEQ ID NO:2) mRNA (Table 2 and 3) Other than breast tissue, Mam001 (SEQ ID NO:2) is detected only in one other tissue type (Testis) and then only in the pooled tissue sample (Table 2) but not in the matched testis cancer samples (Table 3).

Comparisons of the level of mRNA expression in breast cancer samples and the normal adjacent tissue from the same individuals are shown in Table 3. Mam001 (SEQ ID NO:2) is expressed at higher levels in 2 of 11 breast cancer tissues (Mam A06X and Mam 162X) compared with the corresponding normal adjacent tissue. The level of Mam001 (SEQ ID NO:2) expression is lower in breast cancer compared to normal adjacent tissue in four matched samples (Mam B011X, Mam 603X/CO34, Mam 42DN and Mam S123). No expression was detected in one set of matched samples (Mam 47XP). Equivalent levels or very similar levels of expression were detected in four other matched samples (Mam S079, Mam S516, Mam S699 and Mam S997). However increasing cancer mass might in these cases result in an overall increase in the total amount of expression.

The high level of tissue specificity and increased or equivalent expression in 6 of 11 individuals is demonstrative of Mam001 (SEQ ID NO:2) being a diagnostic marker for detection of mammary cancer cells using mRNA.

Measurement of SEQ ID NO:1; Clone ID: 2740238; Gene ID 242151 (Mam002)

The numbers depicted in Table 5 are relative levels of expression in 12 normal tissues of Mam002 (SEQ ID NO:1) compared to Thymus (calibrator). These RNA samples were obtained commercially and were generated by pooling samples from a particular tissue from different individuals.

TABLE 4

Relative levels of Mam002 (SEQ ID NO:1) Expression in Pooled Samples

| Tissue | NORMAL |
|---|---|
| Brain | 0.03 |
| Heart | 0.01 |
| Kidney | 0 |
| Liver | 0 |
| Lung | 0.06 |
| Mammary | 289.01 |
| Muscle | 0 |
| Prostate | 0.31 |
| Small Int. | 0 |
| Testis | 0.08 |
| Thymus | 1.00 |
| Uterus | 0 |

The relative levels of expression in Table 4 show that Mam002 (SEQ ID NO:1) mRNA expression is detected at a high level in the pool of normal mammary but at very low levels in the other 11 normal tissue pools analyzed. These results demonstrate that Mam002 (SEQ ID NO:1) mRNA expression is highly specific for mammary tissue.

The tissues shown in Table 4 are pooled samples from different individuals. The tissues shown in Table 5 were obtained from individuals and are not pooled. Hence the values for mRNA expression levels shown in Table 4 cannot be directly compared to the values shown in Table 5.

The numbers depicted in Table 5 are relative levels of expression of Mam002 (SEQ ID NO:1) compared to thymus (calibrator) in 27 pairs of matching samples. Each matching pair contains the cancer sample for a particular tissue and the normal adjacent tissue (NAT) sample for that same tissue from the same individual. In addition 2 unmatched mammary samples from normal tissues and one unmatched ovarian cancer and one normal (non-cancerous) ovary were also tested.

TABLE 5

Relative levels of Mam002 (SEQ ID NO:1) Expression in Individual Samples

| Sample ID | Tissue | Cancer | Matching | Normal |
|---|---|---|---|---|
| Mam 12X | Mammary Gland | 7.2 | 69 | |
| Mam 42DN | Mammary Gland | 1051 | 2075 | |
| Mam 59X | Mammary Gland | 7.0 | 15.5 | |
| Mam A06X | Mammary Gland | 1655 | 1781 | |
| Mam B011X | Mammary Gland | 32.1 | 2311 | |
| Mam S127 | Mammary Gland | 1.73 | 0 | |
| Mam S516 | Mammary Gland | 9.72 | 69.95 | |
| Mam S699 | Mammary Gland | 83.46 | 75.65 | |
| Mam S854 | Mammary Gland | 133.23 | 836.56 | |
| Mam S967 | Mammary Gland | 59.77 | 188.28 | |
| Mam S997 | Mammary Gland | 94.14 | 73.64 | |
| Mam 162X | Mammary Gland | 674.0 | 31.1 | |
| Mam C012 | Mammary Gland | N/A | N/A | 11379.3 |
| Mam C034 | Mammary Gland | N/A | N/A | 3502.6 |

TABLE 5-continued

Relative levels of Mam002 (SEQ ID NO:1) Expression in Individual Samples

| Sample ID | Tissue | Cancer | Matching | Normal |
|---|---|---|---|---|
| Mam S079 | Mammary Gland | 11772.5 | 903.5 | |
| Mam S123 | Mammary Gland | 3.4 | 170.5 | |
| Ovr 103X | Ovary | 0 | 0 | |
| Ovr 1118 | Ovary | 0.13 | N/A | |
| Ovr 35GA | Ovary | N/A | N/A | 0.13 |
| Utr 23XU | Uterus | 5.6 | 0 | |
| Utr 135XO | Uterus | 0 | 0 | |
| Cvx NK24 | Cervix | 0.9 | 1.4 | |
| End 4XA | Endometrium | 32.2 | 0 | |
| Cln AS43 | Colon | 2.3 | 0 | |
| Cln AS45 | Colon | 0 | 0 | |
| Cln RC01 | Colon | 0.2 | 0 | |
| Lng AC90 | Lung | 0 | 2.0 | |
| Lng LC109 | Lung | 0 | 0.6 | |
| Lng SC32 | Lung | 0.8 | 0 | |
| Sto AC93 | Stomach | 0 | 0 | |
| Tst 39X | Testis | 1.97 | 0 | |

Among 58 samples in Table 5 representing 9 different tissues, the highest expression is seen in mammary tissues. Amongst the non-breast tissues which show expression, only one sample (End 4XA) has expression comparable to that seen in the majority of the breast samples tested. This sample is endometrial tissue, which is a female specific tissue. These results confirm the tissue specificity results obtained with normal samples shown in Table 4. Table 4 and Table 5 represent a combined total of 70 samples in 17 human tissue types. Twenty-two samples representing 11 different tissue types excluding breast had no detected Mam002 (SEQ ID NO:1) mRNA (Table 4 and Table 5).

Comparisons of the level of mRNA expression in breast cancer samples and the normal adjacent tissue from the same individuals are shown in Table 5. Mam002 (SEQ ID NO:1) is expressed at higher levels in 3 of 13 matched breast cancer tissues (Samples Mam S127, Mam 162X and Mam S079) compared with the corresponding normal adjacent tissue. The level of Mam002 (SEQ ID NO:1) expression is lower in breast cancer compared to normal adjacent tissue in eight individuals (Mam 12X, Mam 42DN, Mam 59X, Mam B011X, Mam S516, Mam S854, Mam S967, and Mam S123). Equivalent levels or very similar levels of expression were detected in three other matched samples (Samples Mam A06X, Mam S699 and Mam S997).

The high level of tissue specificity is demonstrative of Mam002 (SEQ ID NO:1) being a diagnostic marker for detection of mammary cancer cells using mRNA. Breast tissue is the only significant source of this gene's expression so far detected. Eight of 13 matched samples have lower levels of expression in cancer than normal adjacent tissue. Thus, decreased expression of this gene appears to be diagnostic of cancer presence.

Measurement of SEQ ID NO:4; Clone ID: 2613064; Gene ID: 27052 (Mam004)

The numbers depicted in Table 6 are relative levels of expression in 12 normal tissues of Mam004 (SEQ ID NO:4) compared to mammary (calibrator). These RNA samples were obtained commercially and were generated by pooling samples from a particular tissue from different individuals.

TABLE 6

Relative levels of Mam004 (SEQ ID NO:4) Expression in Pooled Samples

| Tissue | NORMAL |
|---|---|
| Brain | 0.059 |
| Heart | 0.131 |
| Kidney | 0.018 |
| Liver | 0 |
| Lung | 0.478 |
| Mammary | 1.000 |
| Prostate | 0.459 |
| Muscle | 0.003 |
| Small Intestine | 0.048 |
| Testis | 0.130 |
| Thymus | 0.030 |
| Uterus | 0.071 |

The relative levels of expression in Table 6 show that Mam004 (SEQ ID NO:4) mRNA expression is detected in the pool of normal mammary and also in other tissues including lung, prostate, testis and heart. These results demonstrate that although more highly expressed in normal breast tissue Mam004(SEQ ID NO:4) mRNA expression is not specific for mammary gland.

The tissues shown in Table 6 are pooled samples from different individuals. The tissues shown in Table 7 were obtained from individuals and are not pooled. Hence the values for mRNA expression levels shown in Table 6 cannot be directly compared to the values shown in Table 7.

The numbers depicted in Table 7 are relative levels of expression of Mam004 (SEQ ID NO:4) compared to mammary (calibrator), in 23 pairs of matching samples. Each matching pair contains the cancer sample for a particular tissue and the normal adjacent tissue (NAT) sample for that same tissue from the same individual.

TABLE 7

Relative levels of Mam004 (SEQ ID NO:4) Expression in Individual Samples

| Sample ID | Tissue | Cancer | Matching |
|---|---|---|---|
| Mam 12B | Mammary Gland | 0 | 0 |
| Mam 12X | Mammary Gland | 13.454 | 0 |
| Mam 603X | Mammary Gland | 30.484 | 0 |
| Mam 59X | Mammary Gland | 1.306 | 0 |
| Mam 162X | Mammary Gland | 0.71 | 0.04 |
| Mam 42DN | Mammary Gland | 0.25 | 2.17 |
| Mam S079 | Mammary Gland | 42.18 | 0.47 |
| Mam S123 | Mammary Gland | 0.01 | 0 |
| Mam S516 | Mammary Gland | 1.17 | 0.41 |
| Mam S699 | Mammary Gland | 0.11 | 0.55 |
| Mam S997 | Mammary Gland | 10.43 | 1.29 |
| Sto AC44 | Stomach | 0.61 | 0 |
| Cln SG45 | Colon | 0.04 | 0 |
| Cln TX01 | Colon | 0 | 0 |
| Cvx NK23 | Cervix | 0 | 0 |
| Cvx NK24 | Cervix | 0 | 0 |
| Endo 3AX | Endometrium | 0 | 0 |
| Endo 4XA | Endometrium | 0 | 0 |
| Endo 5XA | Endometrium | 0 | 2.73 |
| Kid 11XD | Kidney | 0 | 0 |
| Kid 5XD | Kidney | 0 | 2.63 |
| Lng C20X | Lung | 0 | 0 |
| Lng SQ56 | Lung | 10.37 | 0 |

Among 46 samples in Table 7 representing 7 different tissues expression is highest in breast tissues particularly cancers. Expression comparable to that seen in breast samples is also seen in 1 of 4 lung samples (Sample 23), 1 of 4 kidney samples (Sample 21) and 1 of 6 endometrial samples (Sample 19). Table 6 and Table 7 represent a combined total of 58 samples in 16 human tissue types. Twenty samples representing 7 different tissue types excluding breast had no detected Mam004 (SEQ ID NO:4) mRNA (Table 6 and Table 7).

Comparisons of the level of mRNA expression in breast cancer samples and the normal adjacent tissue from the same individuals are shown in Table 7. Mam004 (SEQ ID NO:4) is expressed at higher levels in 8 of 11 breast cancer tissues (Mam 12X, Mam 603X, Mam 59X, Mam 162X, Mam S079, Mam S123, Mam S516 and Mam S997) compared with the corresponding normal adjacent tissue. The level of Mam004 (SEQ ID NO:4) expression is lower in breast cancer compared to normal adjacent tissue in two matched samples (Mam 42DN and Mam S699). No expression was detected in one matched sample (Mam 12B).

Elevated expression in the majority of matched cancer samples compared to normal adjacent tissue is indicative of Mam004 (SEQ ID NO:4) being a diagnostic marker for detection of mammary cancer cells using mRNA.

Measurement of SEQ ID NO:3: Clone ID:y155b03; Gene ID: 348845 (Mam005)

The numbers depicted in Table 8 are relative levels of expression in 12 normal tissues of Mam005 (SEQ ID NO:3) compared to testis (calibrator). These RNA samples were obtained commercially and were generated by pooling samples from a particular tissue from different individuals.

TABLE 8

Relative levels of Mam005 (SEQ ID NO:3) Expression in Pooled Samples

| Tissue | NORMAL |
| --- | --- |
| Brain | 0 |
| Heart | 0.0002 |
| Kidney | 0.0001 |
| Liver | 0 |
| Lung | 0 |
| Mammary | 5.4076 |
| Muscle | 0 |
| Prostate | 0 |
| Small Intestine | 0 |
| Testis | 1 |
| Thymus | 0 |
| Uterus | 0 |

The relative levels of expression in Table 8 show that Mam005 (SEQ ID NO:3) mRNA expression is detected in the pool of normal mammary and in testis but is not present at significant levels in the other 10 normal tissue pools analyzed. These results demonstrate that Mam005 (SEQ ID NO:3) mRNA expression is highly specific for mammary tissue and is also found in testis. Expression in a male specific tissue is not relevant in detecting cancer in female specific tissues.

The tissues shown in Table 8 are pooled samples from different individuals. The tissues shown in Table 9 were obtained from individuals and are not pooled. Hence the values for mRNA expression levels shown in Table 8 cannot be directly compared to the values shown in Table 9.

The numbers depicted in Table 9 are relative levels of expression of Mam005 (SEQ ID NO:3) compared to testis (calibrator), in 46 pairs of matching samples. Each matching pair contains the cancer sample for a particular tissue and the normal adjacent tissue sample for that same tissue from the same individual. In addition 2 unmatched mammary samples from normal tissues and one unmatched ovarian cancer and one normal (non-cancerous) ovary were also tested.

TABLE 9

Relative levels of Mam005 (SEQ ID NO:3) Expression in Individual Samples

| Sample ID | Tissue | Cancer | Matching | Normal |
| --- | --- | --- | --- | --- |
| Mam 12X | Mammary Gland | 0.33 | 0.71 | |
| Mam 42DN | Mammary Gland | 0.22 | 0.63 | |
| Mam 59X | Mammary Gland | 0.03 | 0.23 | |
| Mam A06X | Mammary Gland | 70.77 | 0.56 | |
| Mam B011X | Mammary Gland | 0.03 | 1.52 | |
| Mam 162X | Mammary Gland | 0.43 | 0.09 | |
| Mam C012 | Mammary Gland | N/A | N/A | 1.6 |
| Mam C034 | Mammary Gland | N/A | N/A | 2.9 |
| Mam S079 | Mammary Gland | 0.22 | 0.13 | |
| Mam S123 | Mammary Gland | 0.01 | 0.23 | |
| Mam S127 | Mammary Gland | 0 | 0.28 | |
| Mam S516 | Mammary Gland | 0.15 | 0.05 | |
| Mam S699 | Mammary Gland | 0.21 | 0.42 | |
| Mam S854 | Mammary Gland | 1.12 | 0.54 | |
| Mam S967 | Mammary Gland | 30.61 | 0.54 | |
| Mam S997 | Mammary Gland | 0.40 | 0.22 | |
| Mam 14DN | Mammary Gland | 0.07 | 0 | |
| Mam 699F | Mammary Gland | 0.01 | 0.09 | |
| Mam S621 | Mammary Gland | 1.82 | 0 | |
| Mam S918 | Mammary Gland | 6.89 | 1.06 | |
| Cln CM67 | Colon | 0 | 0 | |
| Cln DC19 | Colon | 0 | 0 | |
| Cln AS43 | Colon | 0 | 0 | |
| Cln AS45 | Colon | 0 | 0 | |
| Cln RC01 | Colon | 0.0012 | 0.0003 | |
| Lng AC90 | Lung | 0 | 0 | |
| Lng LC109 | Lung | 0 | 0 | |
| Lng SQ32 | Lung | 0 | 0 | |
| Lng SQ43 | Lung | 0 | 0 | |
| Ovr 103X | Ovary | 0 | 0 | |
| Ovr 1118 | Ovary | 0 | N/A | |
| Ovr A084 | Ovary | 0 | 0 | |
| Ovr G021 | Ovary | 0 | 0 | |
| Ovr 35GA | Ovary | N/A | N/A | 0 |
| Cvx NK23 | Cervix | 0 | 0 | |
| Cvx NK24 | Cervix | 0 | 0 | |
| Endo 3AX | Endometrium | 0 | 0 | |
| Endo 4XA | Endometrium | 0 | 0 | |
| Sto 758S | Stomach | 0 | 0 | |
| Sto AC44 | Stomach | 0 | 0 | |
| Sto AC93 | Stomach | 0 | 0 | |
| Tst 39X | Testis | 0.01 | 0.01 | |
| Utr 85XU | Uterus | 0 | 0 | |
| Utr 135XO | Uterus | 0 | 0 | |
| Utr 23XU | Uterus | 0 | 0 | |
| Kid 124D | Kidney | 0 | 0 | |
| Lvr 15XA | Liver | 0 | 0 | |
| Pan C044 | Pancreas | 0 | 0 | |

TABLE 9-continued

Relative levels of Mam005 (SEQ ID NO:3) Expression in Individual Samples

| Sample ID | Tissue | Cancer | Matching | Normal |
|---|---|---|---|---|
| Skn 448S | Skin | 0 | 0 | |
| Smint 21XA | Small Intestines | 0 | 0 | |

Among 96 samples in Table 9 representing 14 different tissues significant expression is seen only in breast tissues. These results confirm the tissue specificity results obtained with normal samples shown in Table 8. Table a and Table 9 represent a combined total of 108 samples in 18 human tissue types. Sixty-seven samples representing 16 different tissue types excluding breast and testis had either no or very low levels of detected Mam005 (SEQ ID NO:3) mRNA (Table 8 and Table 9).

Comparisons of the level of mRNA expression in breast cancer samples and the normal adjacent tissue from the same individuals are shown in Table 9. Mam005 (SEQ ID NO:3) is expressed at higher levels in 10 of 18 cancer and normal adjacent tissue samples (Mam A06X, Mam 162X, Mam S079, Mam S516, Mam S854, Mam S967, Mam S997, Mam 14DN, Mam S621, and Mam S918) compared with the corresponding normal adjacent tissue. The level of Mam005 (SEQ ID NO:3) expression is lower in breast cancer compared to normal adjacent tissue in eight cancer and normal adjacent tissue samples (Mam 12X, Mam 42DN, Mam 59X, Mam B011X, Mam S123, Mam S127, Mam S699 and Mam 699F). No expression was detected in two matching samples.

The high level of tissue specificity, and overexpression in 10 of 18 matched cancer and normal adjacent tissue samples is indicative of Mam005 (SEQ ID NO:3) being a diagnostic marker for detection of mammary cancer cells using mRNA.

What is claimed is:

1. An isolated antibody that specifically binds a protein encoded by Mam004 (SEQ ID NO:4).

2. A method of imaging breast cancer in a patient comprising administering to the patient an antibody of claim 1 and detecting the antibody in the patient wherein detection of the antibody within the breast allows determination of the presence or absence of cancer in the breast.

3. The method of claim 2 wherein said antibody is labeled with paramagnetic ions or a radioisotope.

* * * * *